United States Patent [19]

Burbank et al.

[11] Patent Number: 5,425,737
[45] Date of Patent: Jun. 20, 1995

[54] SURGICAL PURSE STRING SUTURING INSTRUMENT AND METHOD

[75] Inventors: John E. Burbank, Ridgefield; William J. Allen, Stratford, both of Conn.; George Jessup, Strathfield, Australia; Frederick F. Ahari, Newton, Mass.; Robert A. Rabiner, Middletown, N.J.

[73] Assignee: American Cyanamid Co., Wayne, N.J.

[21] Appl. No.: 89,950

[22] Filed: Jul. 9, 1993

Related U.S. Application Data

[63] Continuation-in-part of Ser. No. 967,033, Oct. 27, 1992, abandoned, which is a continuation-in-part of Ser. No. 865,234, Apr. 8, 1992, abandoned, and Ser. No. 927,969, Aug. 11, 1992, abandoned.

[51] Int. Cl.⁶ ............................................. A61B 17/00
[52] U.S. Cl. .................... 606/144; 606/139; 606/151; 606/207
[58] Field of Search ................. 606/1, 139, 142–144, 606/148, 151, 205–208

[56] References Cited

U.S. PATENT DOCUMENTS

| | | | |
|---|---|---|---|
| 1,982,207 | 11/1934 | Furniss | 606/148 |
| 3,840,003 | 10/1974 | Komiya | 606/151 |
| 4,164,225 | 8/1979 | Johnson et al. | 606/145 |
| 4,532,925 | 8/1985 | Blake, III | 606/143 |
| 4,605,002 | 8/1986 | Rebuffat | 606/148 |
| 4,944,741 | 7/1990 | Hasson | 606/207 |
| 5,100,420 | 3/1992 | Green et al. | 606/143 |
| 5,141,519 | 8/1992 | Smith et al. | 606/205 |
| 5,171,257 | 12/1992 | Ferzli | 606/144 |
| 5,174,276 | 12/1992 | Crockard | 606/142 |
| 5,234,443 | 8/1993 | Phan et al. | 606/144 |
| 5,254,130 | 10/1993 | Poncet et al. | 606/207 |
| 5,275,608 | 1/1994 | Forman et al. | 606/170 |
| 5,330,502 | 7/1994 | Hassler | 606/205 |

FOREIGN PATENT DOCUMENTS

| | | | |
|---|---|---|---|
| 0140557 | 5/1985 | European Pat. Off. | 606/144 |
| 0535370 | 4/1993 | European Pat. Off. | |
| 0370819 | 4/1932 | United Kingdom | 606/148 |

Primary Examiner—Stephen C. Pellegrino
Assistant Examiner—Jeffrey A. Schmidt
Attorney, Agent, or Firm—C. F. Costello, Jr.; M. W. Smith

[57] ABSTRACT

A purse string suturing instrument is provided for quickly and effectively forming a purse string suture in tubular tissue through relatively small cannulas placed in the body. The instrument includes a pair of elongated jaws, each having a row of spaced-apart uniform-size teeth. The jaws are hinged together at one end to clamp the tubular tissue therebetween. The two rows of teeth are offset with respect to each other so that they mesh when the jaws are closed. A single operating mechanism is provided to articulate the pair of jaws with respect to a longitudinal axis of the suturing instrument and actuate the jaws between an open position and a clamping position. The jaws are inserted through a cannula and positioned to close around the tissue to be sutured. The rows of teeth bend the tissue therebetween into a wavelike configuration. A pair of needles, the ends of each being connected to a single length of suture, is then inserted through passageways provided through the teeth. An encircling series of stitches are thus formed in the wall of the tubular tissue to create a purse string suture. The needles and the suturing instrument are then withdrawn through the cannula. The tubular tissue can be snugly fitted over an anastomosis ring or the like by drawing and tying the purse string suture.

23 Claims, 11 Drawing Sheets

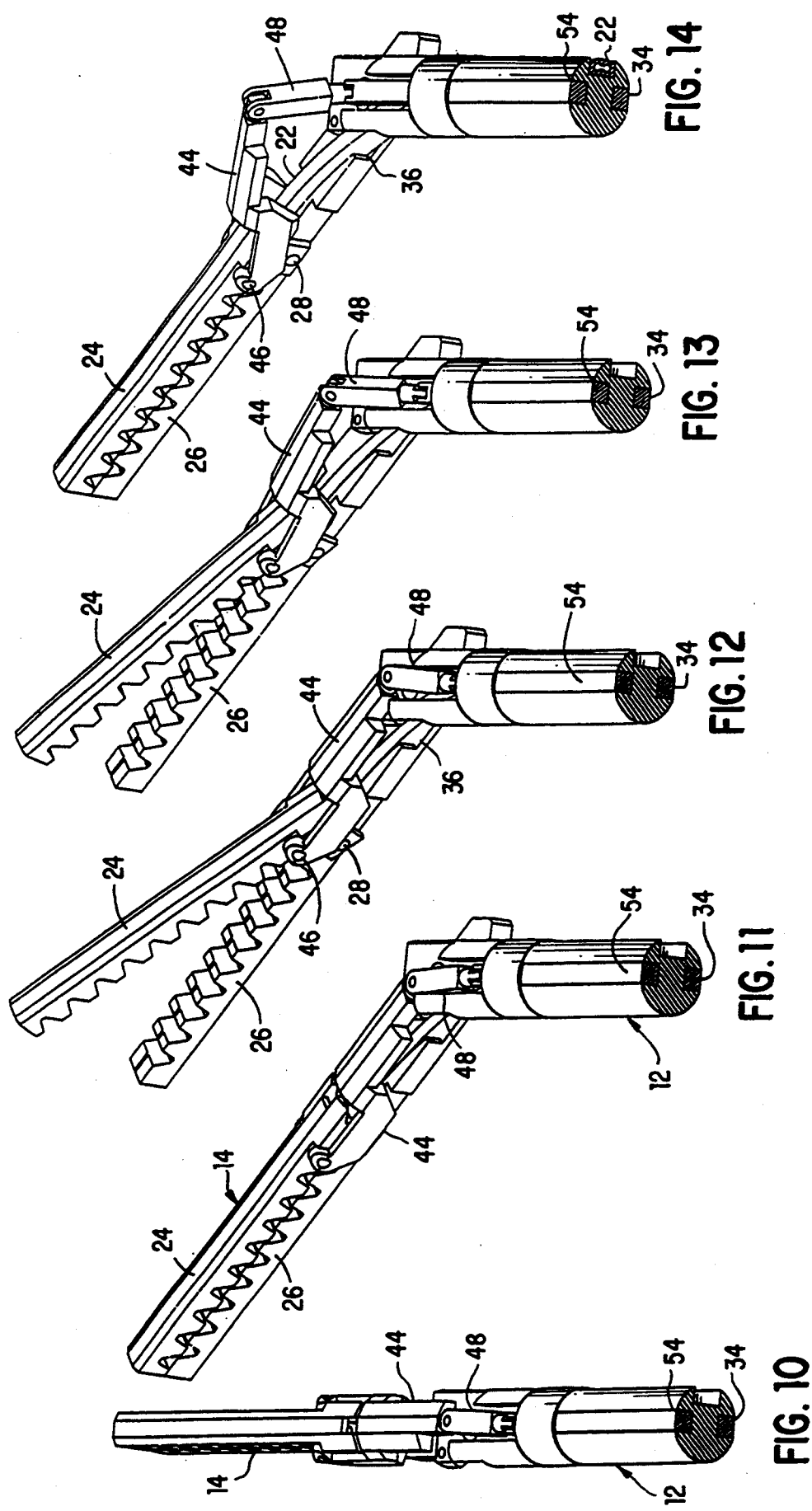

TIMING CHART — PURSE STRING TOOL

OPERATION:
1. START WITH TOOL SET PER LEFT SIDE OF CHART NO 1.
2. INSERT TOOL COMPLETELY THROUGH CANNULA.
3. OPERATE TOOL PER CHART NO 1.
4. INSERT NEEDLE GUIDE AND NEEDLES AND PERFORM PURSE STRINGING.
5. REMOVE NEEDLES AND NEEDLE GUIDE.
6. RESET TOOL TO ORIGINAL CONDITION VIA CHART NO 2.
7. REMOVE TOOL FROM CANNULA.

TIMING CHART - PURSE STRING TOOL

OPERATION:
1. START WITH TOOL SET PER LEFT SIDE OF CHART NO 1.
2. INSERT TOOL COMPLETELY THROUGH CANNULA.
3. OPERATE TOOL PER CHART NO 1.
4. INSERT NEEDLE GUIDE AND NEEDLES AND PERFORM PURSE STRINGING.
5. REMOVE NEEDLES AND NEEDLE GUIDE.
6. RESET TOOL TO ORIGINAL CONDITION VIA CHART NO 2.
7. REMOVE TOOL FROM CANNULA.

SURGICAL PURSE STRING SUTURING INSTRUMENT AND METHOD

BACKGROUND OF THE INVENTION

This application is a continuation-in-part of U.S. patent application Ser. No. 07/967,033, filed Oct. 27, 1992, now abandoned; which is a continuation-in-part of U.S. patent application Ser. No. 07/865,234, filed Apr. 8, 1992 now abandoned and Ser. No. 07/927,969, filed Aug. 11, 1992 now abandoned.

FIELD OF THE INVENTION

The present invention relates to a method of placing a purse string suture in a bowel or other section of tubular tissue and to an instrument for performing the procedure quickly and without having to open the patient completely.

It is sometimes necessary in performing operations on sections of the alimentary canal to have to put a purse string suture in that tubular tissue. This occurs, for example, when the severed ends of the bowel are rejoined by anastomosis. A biofragmentable anastomosis ring is used to provide a mechanically locking connection that maintains contact between the ends of the intestine in an inverted anastomosis. A purse string suture is used to draw each of the severed ends of the intestine snugly around the barrel of the ring. The ring produces secure serosa-to-serosa apposition of the ends of the intestine and maintains a satisfactory patency until healing occurs and the ring degrades into small harmless fragments, which are eliminated from the body. Anastomosis rings are used in the treatment of various disease processes for which intestinal resection and anastomosis is indicated, for example, carcinoma, diverticular disease, and colostomy closure. A description of the procedure may be found, for example, in U.S. Patent Nos. 4,467,804; 4,552,148 and 4,766,898.

Placing a purse string suture in tubular tissue has generally required fully opening the body cavity. It would be desirable if there were a procedure for doing so without such a large incision, for example by accessing the body cavity through one or two cannulas instead.

SUMMARY OF THE INVENTION

It is a principal object of the present invention to provide a method and instrument for quickly and effectively putting a purse string suture in a bowel or other section of tubular tissue.

It is a further object of the invention to provide a method and means for putting a purse string suture in a tubular tissue using techniques known as least or minimally invasive surgery without having to fully open the body cavity.

It is a further object of the invention to provide a purse string suturing instrument with an operating mechanism that can be simply and easily manipulated to operate the suturing instrument.

These and other objects are achieved by use of the surgical purse string suturing instrument of the present invention.

In one aspect of the present invention, a suturing instrument is comprised of an elongated shaft; a pair of relatively movable jaws for clamping the tubular tissue therebetween, the first jaw being substantially pivotable with respect to the second jaw about a first pivot axis, and each jaw having a row of spaced-apart, uniform-size teeth; a mechanism for articulating the pair of jaws about a second pivot axis orthogonal to the first pivot axis; a mechanism for closing the jaws together to clamp the tubular tissue therebetween; and an operating mechanism for operating the articulating mechanism and the closing mechanism. The tubular tissue is clamped by meshing the row of teeth of the first jaw with the row of teeth of the second jaw to bend the tissue therebetween into a wavelike configuration with the collapsed tube forming a two-wall thickness of tissue overlying the crest of each tooth. The two rows are opposed and offset with respect to each other so that the rows of teeth mesh when the jaws are closed.

Cut into the crest of each tooth is a channel that runs parallel to the direction of the row of teeth. All of these channels in each row are aligned so as to define a substantially straight passageway at their bottoms, which is segmented or interrupted by the gaps between the teeth. This passageway permits the transit of a thread-pulling needle through all of the teeth in the row. The bottom of the segmented channel is sufficiently close to the bases of the teeth that when a needle is forced through the passageway, with the jaws clamped across the tissue, the needle can pierce and run through the wall of the wave of tissue overlying and contacting the crest of each tooth but avoid penetrating the next adjacent wall of tissue. In this way, the needle threads the suturing material through only the wall of tissue that contacts the teeth through which the needle passes, and does not sew the tube closed. By forcing two needles attached to opposite ends of a length of suturing thread material completely through passageways formed by the channels in each row of teeth in the tissue, an encircling series of stitches is created in the wall of the tubular tissue. Preferably, each needle can be snapped-off near the suture and the needle heads and the suture can be withdrawn from the body through a cannula while the needle shafts are withdrawn back through the passageways. The jaws of the instrument can then be opened and the tissue released. The jaws are closed again to withdraw the suturing instrument through another cannula in the body. The ends of the suture are cut from the needle head and drawn snugly around an anastomosis ring or the like and knotted to form a purse string suture.

Because the needle passageway is the bottom of a channel cut into the crest of each tooth, when the jaws are opened the suturing thread slides through the channels and free of the teeth. Preferably, the cross-section of the channel through each tooth is substantially keyhole shaped. The round section is at the bottom of the channel and the narrower width slot section extends from the round section to the crest of the tooth. Using this preferred embodiment, needles having a diameter small enough to fit through the round section but too large to enter the slot can be used. This serves to hold the needle in the desired position at the bottom of the channel, while allowing the smaller-diameter thread to be released when the jaws are opened.

A preferred actuating mechanism for opening and closing the pair of jaws includes a driving rod for pivoting the first and second jaws about the first pivot axis. The driving rod is connected to one of the jaws through a lost motion lever for raising and lowering that jaw about a third pivot axis parallel to the first pivot axis. The first and third pivot axes are offset from one another.

It is also preferred that the articulating mechanism includes a camming rod for abutting one of the jaws and pivoting the pair of jaws about the second pivot axis. The articulating mechanism also includes stop means for limiting the articulating movement of the jaws.

It is desirable that the operating mechanism include a rotatable knob connected to an axially slidable actuating sleeve by mutually engagable threads. The knob can be rotated to sequentially actuate the articulating mechanism to position the pair of jaws near the tissue to be clamped and then actuate the actuating mechanism to clamp the pair of jaws about the tissue.

It is also preferred that the suturing instrument includes sealing means for providing an airtight seal within a cannula receiving the suturing instrument.

In accordance with another aspect of the invention, a surgical suturing instrument is comprised of a pair of relatively movable jaws for clamping tubular tissue therebetween, a first jaw of the pair of jaws being pivotable with respect to a second jaw about a first pivot pin, with each jaw having a row of spaced-apart, uniform-size teeth, and an actuating mechanism actuating the pair of jaws between an open position for receiving the tubular tissue and a clamping position where the row of teeth of the first jaw meshes with the row of teeth of the second jaw. The actuating mechanism includes a lost motion linkage having a lever pivotally connected to one of the jaws about a second pivot pin parallel to the first pivot pin, a link pivotally connected to the lever and a driving rod pivotally connected to the link, and a camming rod slidably disposed to engage one of the jaws and pivot the pair of jaws about a third pivot pin transverse to the first pivot pin. Also provided is an operating mechanism connected to the actuating mechanism and the camming rod, the operating mechanism being actuating to slide the camming rod and articulate the pair of jaws about the third pivot pin transverse to the first pivot pin and to actuate the actuating mechanism to open and close the pair of jaws about the first pivot pin.

In accordance with yet another aspect of the invention, a method of placing a purse string suture in a section of tubular tissue includes the steps of inserting a cannula into the body cavity, and inserting, through the cannula, an instrument comprising a pair of relatively movable jaws hinged together at one end for pivotal movement about a first axis, with each jaw having a row of spaced-apart, uniform-size teeth, each tooth having a base and a crest, the two rows being opposed and offset with respect to each other so that the rows of teeth have a channel therein running parallel to the direction of the row, and all of the channels in each row are aligned so as to define at their bases a substantially straight needle passageway through all of the teeth in the rows, the pair of jaws being closed. An operating mechanism is actuated to first articulate the pair of jaws about a second pivot axis transverse to the first pivot axis and then actuate the first and second jaws to pivot about the first axis to an open position. The first and second jaws are positioned adjacent and transverse to the section of tubular tissue, and the operating mechanism is actuated to pivot the first and second jaws to pivot about the first axis to clamp around the tissue and bend the clamped tissue into a wavelike configuration with a two-wall thickness of the tissue overlying the crest of each tooth, the tissue being forced deep enough into the spaces between the teeth that a first wall thickness of tissue, but not the second wall thickness thereof, protrudes into the needle passageway. A suturing cartridge having two needles attached to opposite ends of a length of bioabsorbable thread is loaded into a needle cartridge through a pathway in one of the jaws, and the two needles are forced completely through the needle passageways and the tissue, one needle for each passageway, thereby creating an encircling series of stitches in the wall of the tubular tissue. The needles are detached from the thread and removed from the body, thereby leaving a purse string suture in the tubular tissue, ready to be drawn snug and tied.

These and other objects, aspects, features, and advantages of the present invention will become apparent from the following detailed description of the preferred embodiments taken in conjunction with the drawings.

BRIEF DESCRIPTION OF THE DRAWINGS

FIG. 10 is an isometric view of the distal end of the purse string suturing instrument showing the pair of jaws in an unarticulated and closed position;

FIG. 11 is an isometric view of the distal end of the purse string suturing instrument showing the pair of jaws in an articulated and closed position;

FIG. 12 is an isometric view of the distal end of the purse string suturing instrument showing the pair of jaws in an articulated and fully open position;

FIG. 13 is an isometric view of the distal end of the purse string suturing instrument showing the pair of jaws in an articulated and partially open position;

FIG. 14 is an isometric view of the distal end of the purse string suturing instrument showing the pair of jaws in an articulated and fully clamped position;

DESCRIPTION OF THE PREFERRED EMBODIMENTS

Figure 1:
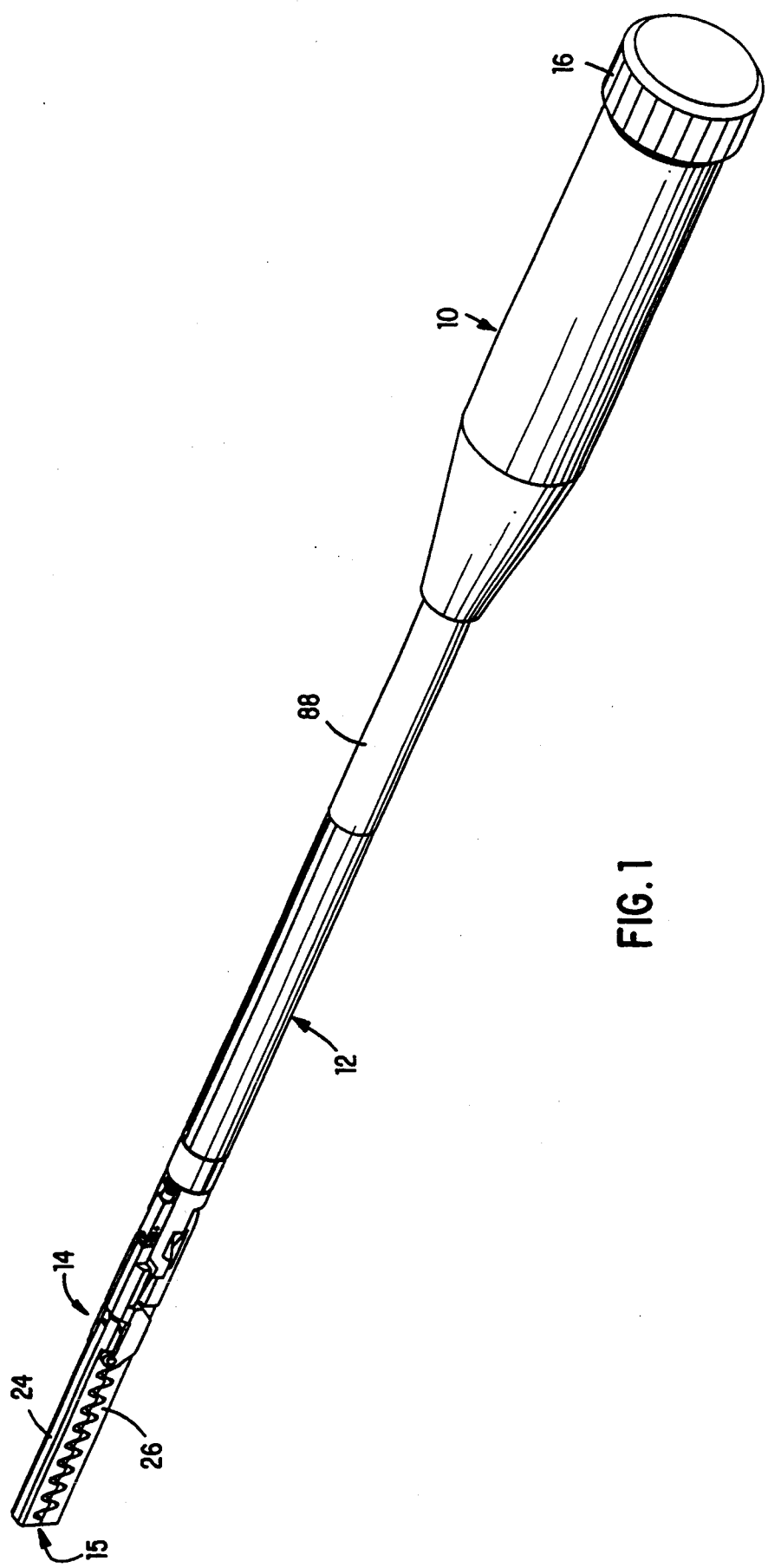
FIG. 1 is an isometric view of a purse string suturing instrument in accordance with the present invention.
Figure 2:
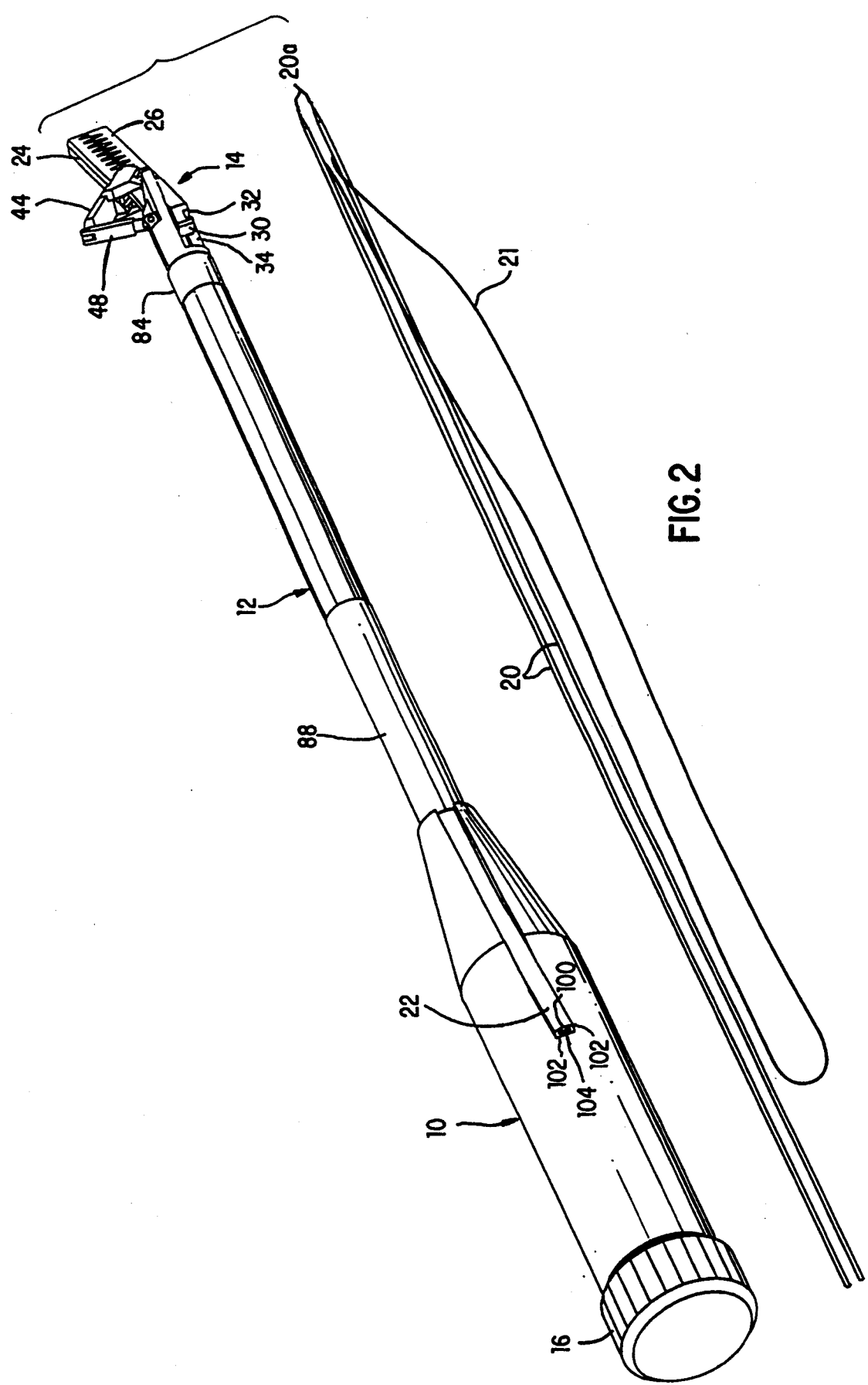
FIG. 2 is an isometric view of the purse string suturing instrument in accordance with the present invention illustrating a pair of jaws in the articulated and clamped position and two needles and a connecting thread of the type used in the present invention.

FIGS. 1 and 2 are isometric views of the purse string suturing instrument of the present invention.

The three main portions of the purse string suturing instrument are comprised of a proximal handle section 10, an elongated middle section 12 and a distal jaw section 14 having a pair of jaws 15. Generally speaking, the jaw section positioned as shown in FIG. 1 and the middle section are inserted into the body through a well-known cannula (not shown), and then a rotatable knob 16 on the handle section is operated to position the pair of jaws to clamp a portion of tissue that is to receive a purse string suture.

FIG. 2 is a view of the suturing instrument with the pair of jaws in an articulated and clamped position that will be discussed in detail below. FIG. 2 also shows one type of suturing needle to be used in the purse string suturing instrument of the present invention. Each end of a single length of preferably bioabsorbable, monofilament suture or thread 21 is attached to tip end 20a of a needle 20. Both needles are inserted into a needle cartridge 22 in a manner that will be described below. One type of preferred surgical needle used in the surgical suturing instrument of the present invention is disclosed in application Ser. No. 07/967,033, and that application is incorporated herein by reference.

Figure 3:
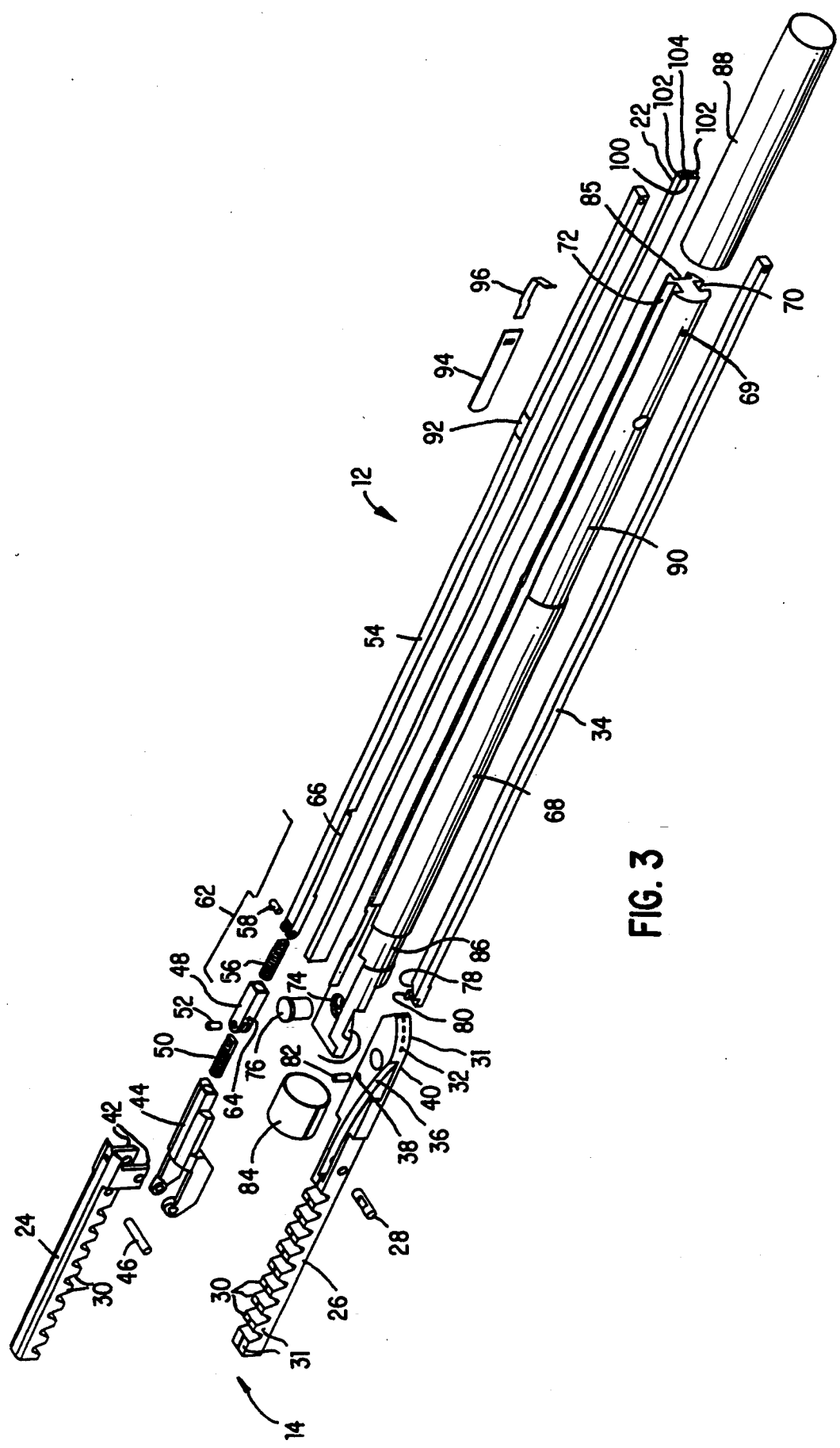
FIG. 3 is an exploded isometric view of a distal end section and a middle section of the purse string suturing instrument of the present invention.
Figure 4:
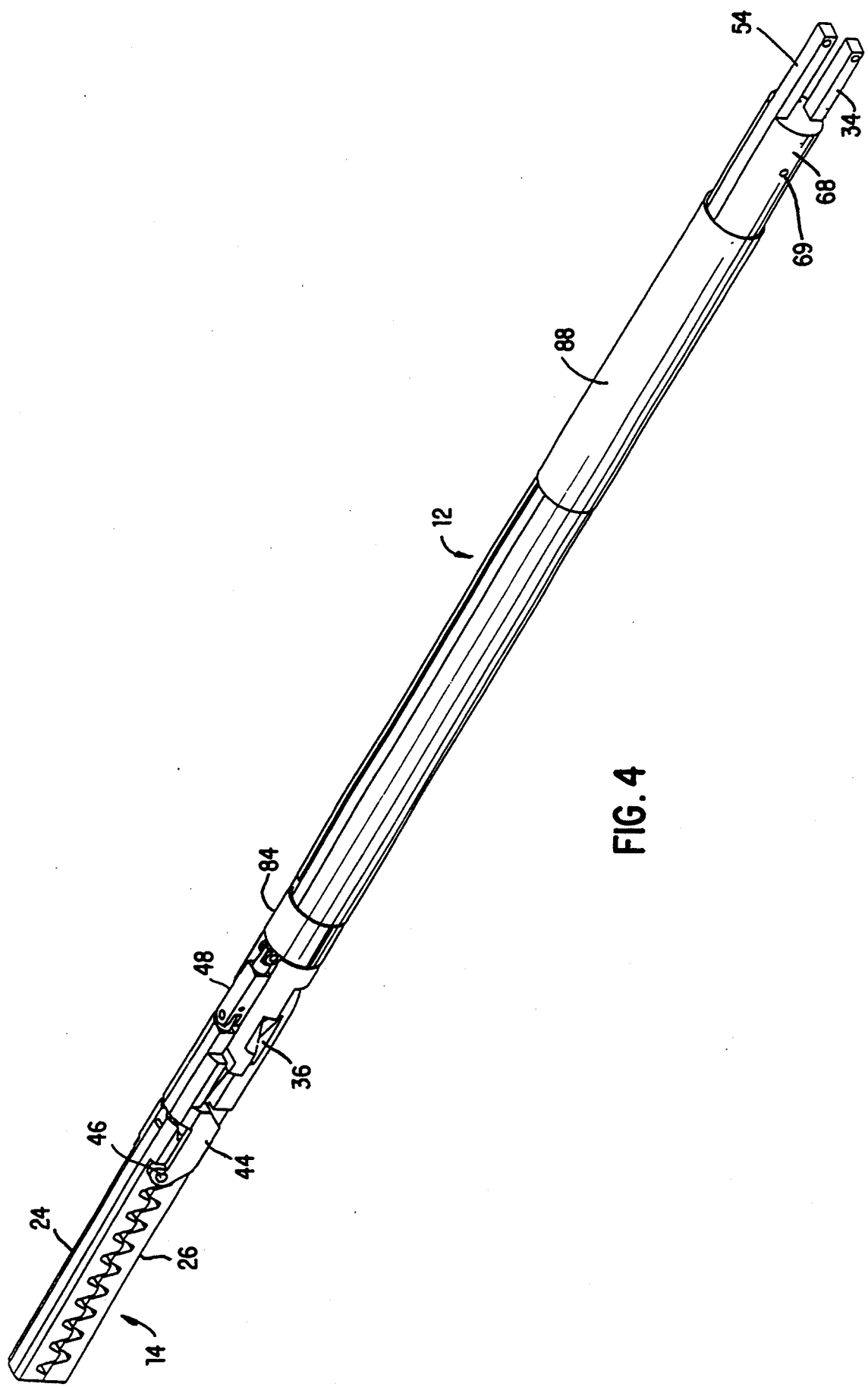
FIG. 4 is a partial isometric view of the purse string suturing instrument in its quiescent condition with the jaws in a closed position, ready to be inserted through a cannula.

FIGS. 3 and 4, respectively, are an exploded view and an assembled view of the distal jaw section 14 and the elongated middle section 12 of the purse string suturing instrument. This jaw section and its components are substantially similar to that disclosed in application Ser. No. 07/967,033 in connection with FIGS. 27 through 32. The jaw section comprises a first jaw 24 and a second jaw 26 connected by a pivot pin 28 for pivoting movement about a first axis. Each jaw includes a row of space-apart teeth 30 of uniform size and spacing. The teeth of the first and second jaws are offset from each other so that when the first, or upper, jaw 24 is swung around the pivot pin to the closed position opposed to the second, or lower, jaw, the teeth mesh with each other. A channel 31 is formed in the crest of each tooth. Each channel runs parallel to the direction of the row of teeth. In cross-section, each channel is shaped like a keyhole including a circular portion at its bottom, i.e., the location most distant from the crest of the tooth in which the channel is formed, and a rectangular portion or slot extending from the circular portion to the crest of the tooth. The circular portions of channels of both rows of teeth are aligned so as to form a substantially straight passageway, which is segmented or interrupted by the gaps between the teeth.

As best seen in FIG. 3, the second jaw 26 includes at its proximal end an exterior camming surface 33 and an interior camming surface 32, and is positioned to be abutted by a sliding camming rod 34. In addition, the second jaw has a curved pathway 36 for receiving the needle cartridge 22, a small hole 38 for receiving a limit pin and a large hole 40 for receiving a pivot pin in a manner discussed in detail below.

The first jaw 24 has at its proximal end extensions 42 to be connected to lower jaw 26 by pivot pin 28. The lost motion lever 44 connects to upper jaw 24 by pivot pin 46 for pivoting movement about a second pivot axis parallel to the first pivot axis. The lost motion lever is connected to a link 48 by a first coupler 50 and a link pin 52. The link 48 is also connected to a driving rod 54 by a second coupler 56 and link pin 58. As will be appreciated, each coupler 50 and 56 has one end that is cylindrical. This allows the link 48 to rotate, or twist, about its longitudinal axis as it pivots about both link pins. However, a spring wire 62 is connected between a first pin hole 64 in the link and a second pin hole 66 on the driving rod 54 to provide a restoring torque and bias the link to its untwisted position.

The middle section 12 is comprised of an elongated shaft 68 for slidably housing the camming rod 34 and driving rod 54 in elongated slots 70 and 72, respectively. The distal end of the shaft 68 has a large hole 74 for receiving an articulating pin 76. The pin 76 extends into the large hole 40 in the second jaw 26 to allow the pair of connected jaws 24 and 26 to pivot about a third pivot axis, substantially perpendicular to the first pivot axis, when the camming rod 34 either pushes the second jaw 26 through contact between the exterior camming surface 33 and a camming surface 78 on the camming rod or pulls the second jaw by way of contact between the interior camming surface 32 and a camming pin 80 on the camming rod. A limit pin 82 extends from the small hole 38 in the second jaw to limit articulation of the jaws about the third pivot axis by engaging an unshown groove in the underside of the elongated shaft 68. The shaft also includes an elongated slot 85 for receiving the needle guide, or cartridge, 22.

A split sleeve 84 slips over the distal end of the elongated shaft 68 into a reduced section 86 thereof to contain the distal ends of the camming rod, the driving rod and the needle guide within their respective slots. At the proximal end of the shaft 68, a sleeve 88 fits over another reduced section 90 to contain the proximal ends of the camming rod, the driving rod and the needle cartridge. The sleeve 88 also acts as an air seal to prevent air from exiting or entering the body. The airtight seal is accomplished by providing the driving rod 54 with a raised area 92 that contacts the inner surface of sleeve 88. The camming rod is provided with the same type of raised area (not shown). Since the needle cartridge 22 is normally not inserted in the shaft 68 until after the suturing instrument is inserted into the body through the cannula, a flap 94 and spring 96 are positioned in the needle cartridge slot 84 and press against the inner surface of sleeve 88 to maintain an airtight seal.

Figure 5:
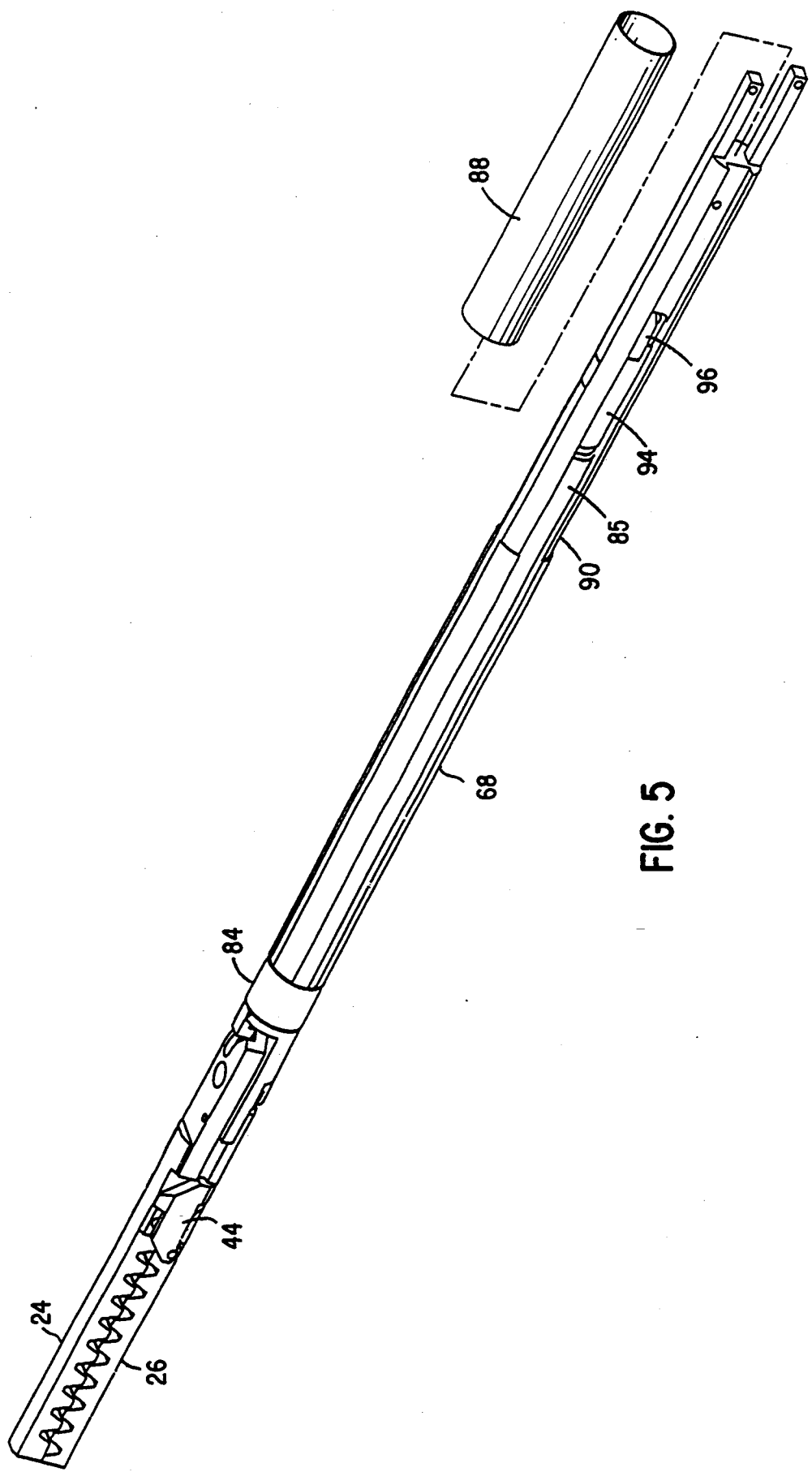
FIG. 5 is an isometric view of the purse string suturing instrument illustrating a sleeve to be fit over part of the middle section.

FIG. 5 shows the elongated shaft 68 with the sleeve 88 removed and without the needle cartridge 22. The flap 94 positioned in the needle cartridge slot 85 is biased radially outwardly by the spring 96 so as to substantially abut the inner surface of the sleeve and prevent air from passing through the slot 85. When the needle cartridge is inserted into the slot 85 it depresses the flap and spring and slides in the axial direction through the suturing instrument.

The needle cartridge 22, as best seen in FIGS. 2 and 3, is made of flexible material, e.g., a suitable polymer plastic, and includes an opening 100 extending in the axial direction through its elongated body. The opening is designed to receive two surgical needles 20 and a bioabsorbable surgical thread 21 connected at each end to one of the needles to form a closed loop as shown in FIG. 2. The opening 100, therefore, has a substantially "dog-bone" cross-section comprising two circular sections 102 joined by a channel 104. A surgical needle is loaded into each circular section. As will be appreciated, the channel is designed to have a width smaller than the diameter of the needles so the needles cannot slide laterally out of their respective circular sections. As the needles travel axially within the opening as described in detail below, the surgical thread follows the needle by passing through the channel.

Figure 6:
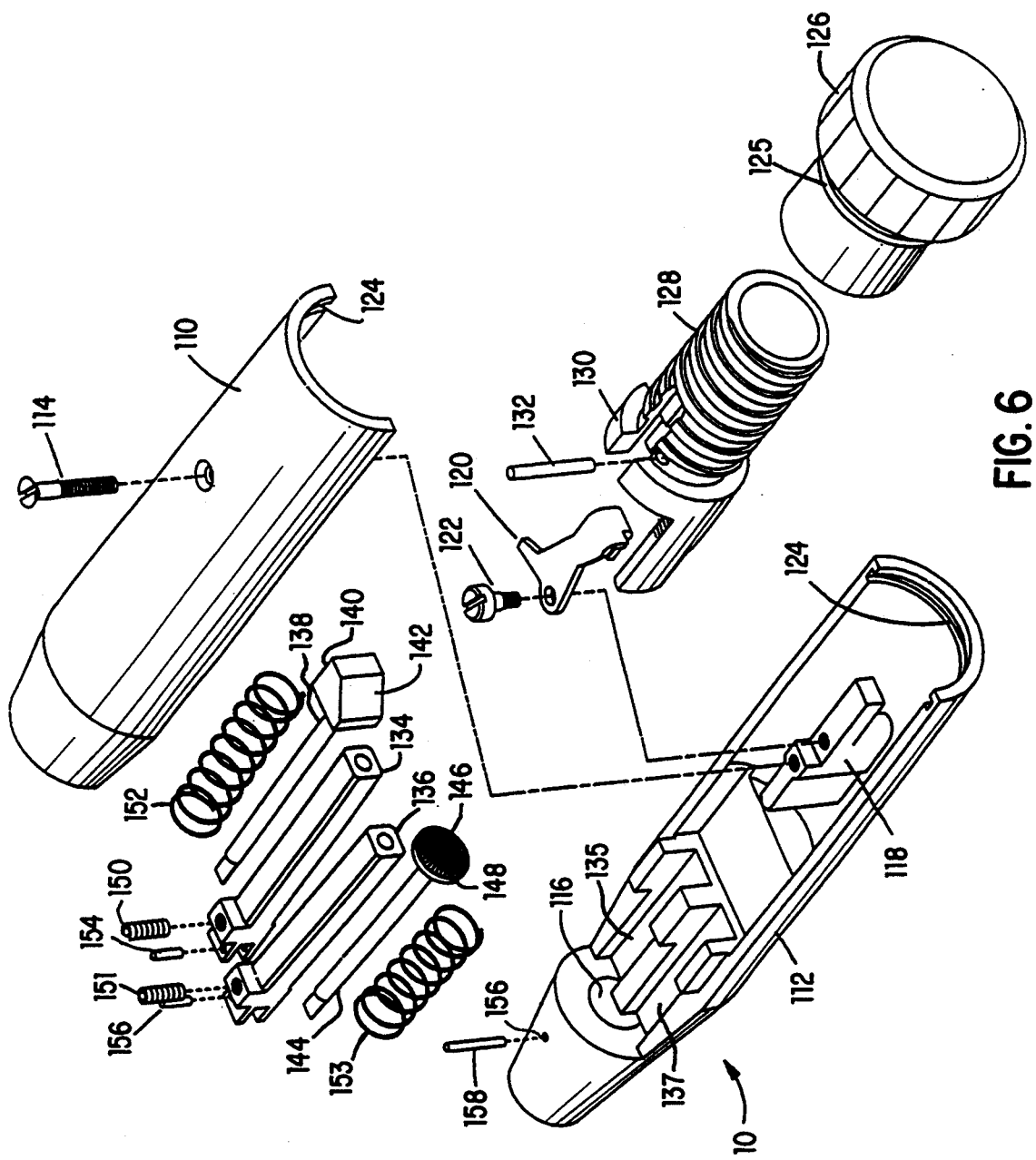
FIG. 6 is an exploded isometric view of a proximal end section of the purse string suturing instrument of the present invention illustrating an operating mechanism.

The handle section 10 is shown in exploded isometric view in FIG. 6. The handle section is comprised of upper and lower body halves 110 and 112 that are secured together by a single screw 114. The upper body half 110 includes a small protrusion (not seen in FIG. 6) in its front portion, or distal end, that keys into opening 116 in the lower body half 112 to align the body halves. The lower body half 112 includes a stationary post 118 for receiving the screw 114 and for pivotally mounting a lever 120 by means of a pivot screw 122. The rear end of both body halves each has an arcuate slot 124 for receiving an annular rib 125 on a rotatable knob 126. The knob includes internal threads for receiving external threads 128 of a hollow cylindrical actuating sleeve 130. The actuating sleeve is keyed to post 118 so it cannot rotate, but rather is moved axially back and forth by rotation of the knob. A pin 132 is press-fitted through the actuating sleeve 130 and bears against lever 120 as the actuating sleeve moves in a manner described below.

The front end of the handle section is equipped with first and second elongated menders 134 and 136 that are slidably disposed in slots 135 and 137, respectively, in the lower body half 112 of the handle section. The first member 134 has an axial opening for receiving a first connecting rod 138. The connecting rod includes at one end a box-shaped head 140 with an angled face 142 and is secured in the first member at the other end by a screw 150. A second connecting rod 144 fits within an axial opening in the second elongated member 136. The second connecting rod has a conically-shaped head 146 and is secured within the second member at the other end by a screw 151. First and second compression springs 152 and 153 fit over the elongated members and provide a restoring force to bias the connecting rods toward the rear of the handle section. The first elongated member 134 is connected to driving rod 54 by pin 154 and the second elongated member 136 is connected to camming rod 34 by pin 156. A connecting pin 158 extends through a hole 159 in the lower half 112 of the handle and a hole 69 in the extended shaft 68 (see FIG. 3) to secure the handle section 10 to the middle section 12. The inner working mechanisms of the handle section described above together serve as motion imparting means to impart rotational movement of the knob to linear movement of the driving rod 54 and camming rod 34.

Figure 7:
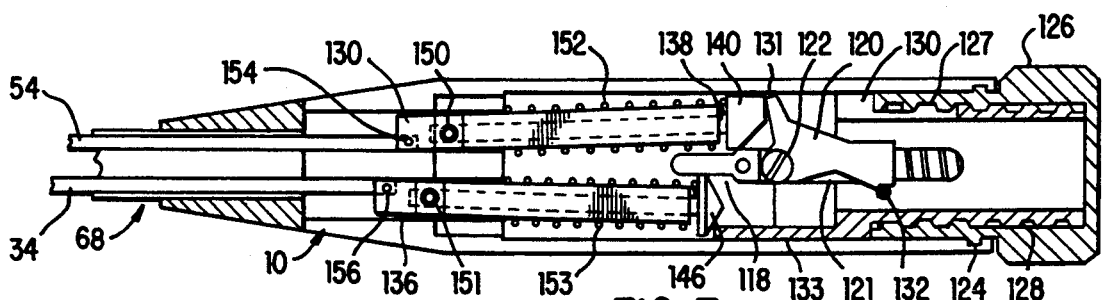
FIG. 7 is a cross-sectional view of the operating mechanism in a fully withdrawn position.
Figure 8:
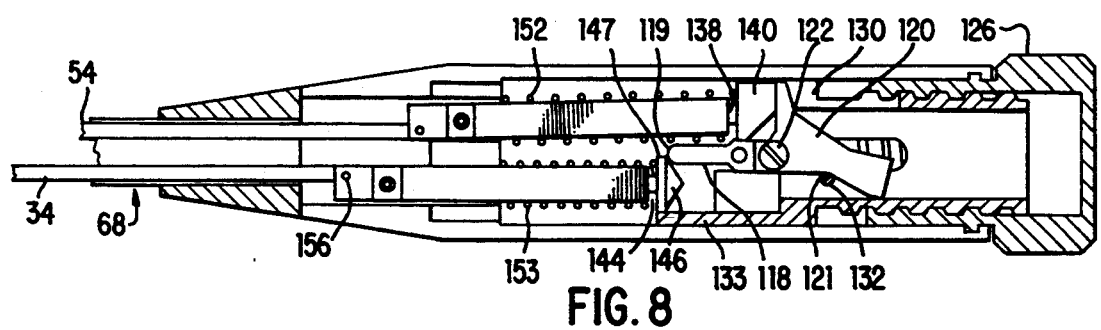
FIG. 8 is a cross-sectional view of the operating mechanism in an intermediate position.
Figure 9:
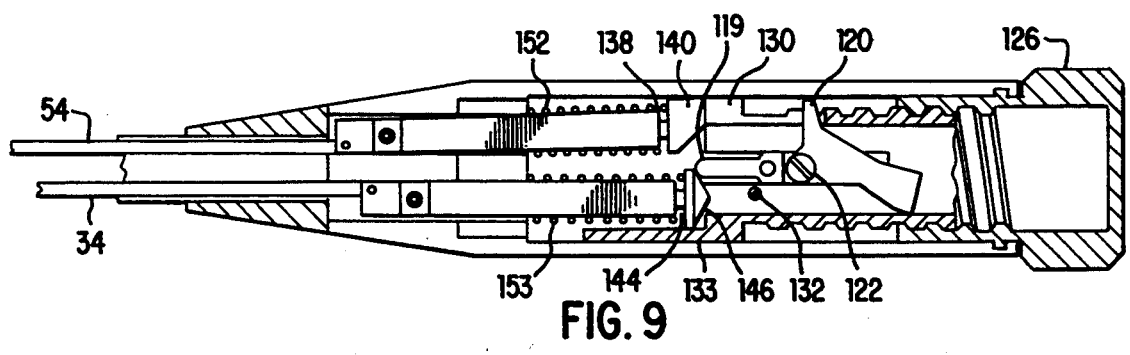
FIG. 9 is a cross-sectional view of the operating mechanism in a fully extended position.

Having identified the individual components of the purse string suturing instrument, its operation will be explained below with reference primarily to FIGS. 7 through 14. FIGS. 7 through 9 are cross-sectional views of the handle section showing the actuating sleeve 130 at three different positions. FIGS. 10 through 14 illustrate the distal end of the suturing instrument with the jaw section in different positions.

When the suturing instrument is prepared to enter the body through a cannula, the jaw section 14 is in the unarticulated position, i.e., axially aligned with the middle section 12, as shown in FIG. 10. In this "entry" position the actuating sleeve 130 is fully retracted as shown in FIG. 7, i.e., in the rearward most position within the knob 126. The pin 132 is positioned at the tail section of lever 120 and holds an arm 131 of the lever against the head 140 of the first connecting rod 138 which in turn contacts compression spring 152. This forward holding force applied to the first connecting rod holds driving rod 54 in an intermediate position to keep the jaw section closed. With the actuating sleeve fully retracted, an extension 133 of the actuating sleeve is positioned immediately opposite the conical head 146 of the second connecting rod.

Actuation of the suturing instrument is initiated by rotating the knob 26 in a first direction. Internal threads 127 on the knob mesh with threads 128 on the actuating sleeve to axially move the actuating sleeve toward the front end of the handle mechanism. The forward movement of the actuating sleeve initially drives extension 133 into the conical head 146 to advance the second connecting rod and camming rod in the forward direction. With reference to FIG. 3, this action presses camming surface 78 against the exterior camming face 32 on the second jaw 26 to articulate the jaw section about articulating pin 76. This articulated position of the jaw section is illustrated in FIG. 11.

As the actuating sleeve continues forward by rotation of the knob, pin 132 slides into a notched portion 121 of the lever 120 as shown in FIG. 8, allowing it to rotate in the clockwise direction about pivot screw 122 by the force of compression spring 152. Rearward movement of the first connecting rod pulls driving rod 54 and, in turn, the link 48 and lost motion lever 44 rearwardly to pivot the first jaw 24 about pivot pin 28 and open the jaw section 14 as shown in FIG. 12. At this point the extension 133 of the actuating sleeve has driven a base 147 of head 146 of the second connecting rod 144 past a nose portion 119 of stationary post 118. The conical shape of the head 146 allows it to slide upwardly and rest against the nose portion 119 as the second member pivots slightly about pin 156, thus allowing the extension 133 to continue its forward motion. As long as the extension 133 extends beneath the conical head 146, the second connecting rod 144 and camming rod 34 are effectively restricted from moving and lock the jaw section 14 in its articulated position, preferably angled at about 40° as regulated by stop pin 82. When the jaw section 14 is positioned as shown in FIG. 12, the suturing instrument can be manipulated to position the tissue to be clamped between the pair of jaws.

As the knob continues to rotate, the actuating sleeve 130 abuts head 140 and pushes the first connecting rod and driving rod 54 in the forward direction to close and clamp the jaw section 14 as shown in FIGS. 13 and 14. As the driving rod 54 moves forwardly, the link 48 rotates approximately 90° about its longitudinal axis as can be seen from viewing FIGS. 12 through 14.

Figure 15:
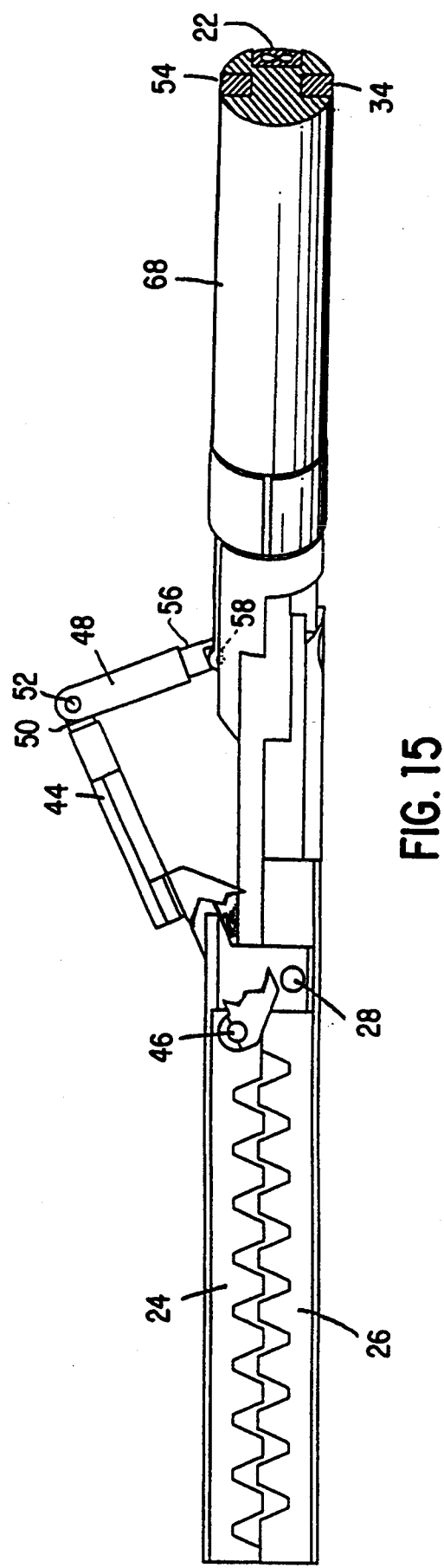
FIG. 15 is a side view of the distal end of the purse string suturing instrument in the same position shown in FIG. 14.

FIG. 15 is an elevational view of clamped jaw section positioned as shown in FIG. 14. With the driving rod 54 in its fully forward position, a pivot point is created about pivot pin 58 linking the second universal pin 56 (connected to the link 48) and the driving rod 54. Another pivot point is created about pivot pin 52 linking the first universal pin 50 (connected to the toggle or lost motion lever 44) and the link 48. By virtue of the raised lost motion lever, which creates a longer (and greater) moment arm about the fulcrum at pin 28, a significant clamping force can be achieved by the pair of jaws to tightly squeeze the tissue therebetween.

The needle cartridge 22 is preferably positioned in the shaft of the suturing instrument once the jaws are clamped around the tissue. The needle cartridge can then be pushed forwardly to extend into the curved pathway as shown in FIG. 14 and be positioned with its distal end against the front row of teeth in the jaws. At this position, the circular portions 102 of the opening 100 in the needle cartridge are aligned with the passageways formed in the teeth.

The surgical needles and suture connected thereto can then be forced forwardly into the passageways to pierce the wall of tissue that contacts the teeth of that jaw without penetrating the second wall of tissue. In this manner, each needle threads the suture through one wall of the two-wall thickness of the tissue and does not sew the tube closed. Preferably, the heads of the needles are snapped-off using forceps and withdrawn, with the suture, through a second cannula providing access into the body cavity.

To remove the suturing instrument from the body after the stitches have been placed in the tissue, the knob 126 is rotated in the reverse direction to retract the actuating sleeve 130. This initially allows the first connecting rod 138 and driving rod 54 to move rearwardly by the force of compression spring 152 and open the jaws to release the tissue. The link 48 and lost motion lever 44 are lowered to their normal position by this movement. As the actuating sleeve continues to be retracted by rotation of the knob, pin 132 moves rearwardly and begins to force the lever in the counterclockwise direction about pivot screw 122 to slightly advance the first connecting rod 138, via head 140, and driving rod 54 to close the pair of jaws. This rearward movement of the actuating sleeve also withdraws extension 133 from beneath head 146 of the second connecting rod 144, allowing it to slide downwardly and out of contact with nose portion 119. The head 146 is then biased in the rearward direction by compression spring 153 against the extension 133 and continues to move rearwardly as the actuating sleeve is retracted. The compression spring pushes the second contacting rod 144 and camming rod 34 in the rearward direction to straighten the jaw section to its unarticulated position as shown in FIG. 10. This is accomplished by a pulling force applied by camming rod 80 on the interior camming surface 32 of the second jaw. The suturing instrument can then be withdrawn through the cannula and removed from the body.

Figure 16A:
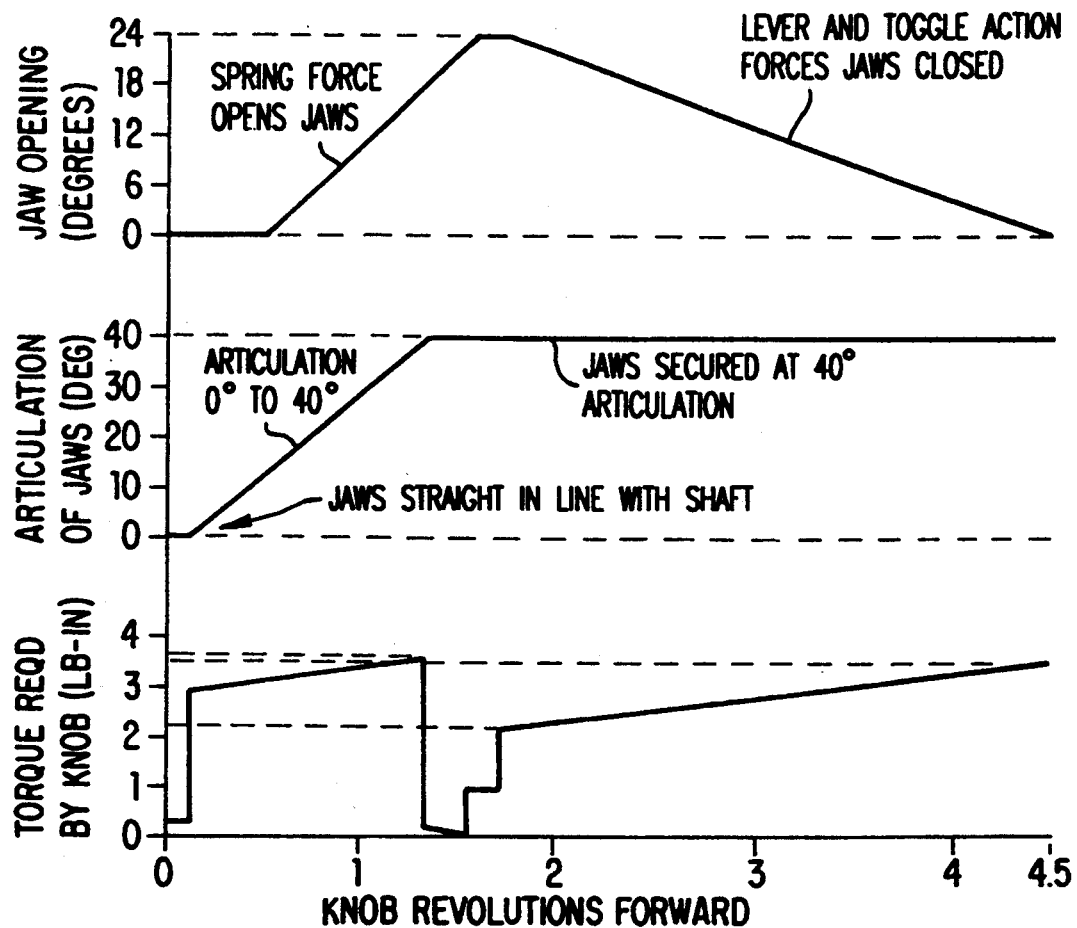
FIG. 16 illustrates two timing charts showing the timing of operating a rotatable knob in both the forward and reverse directions.
Figure 16B:
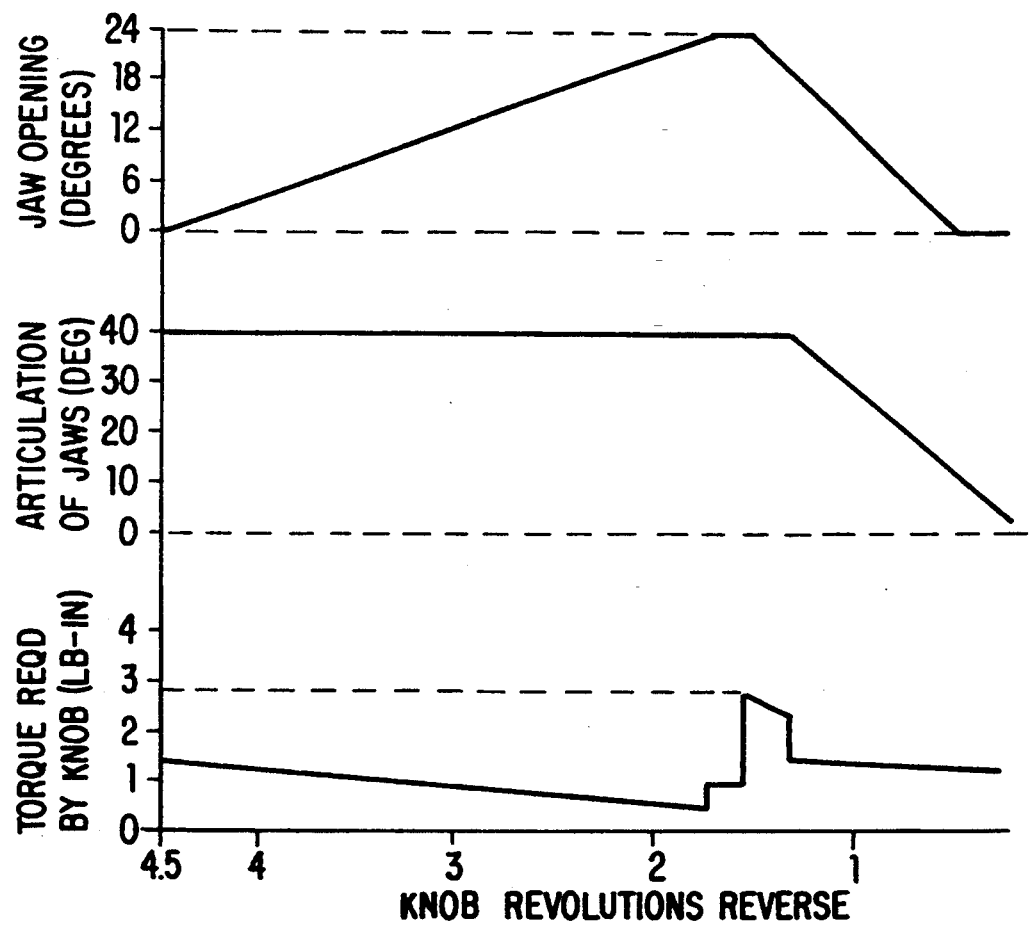

FIG. 16 illustrates timing charts 1 and 2 displaying the timing of knob revolutions vs. torque required by the knob, articulation of the jaws and the degree of jaw opening in connection with operation of the purse string suturing instrument in accordance with the preferred embodiment of the present invention as discussed above.

Although a specific embodiment of the present invention has been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A method of placing a purse string suture in a section of tubular tissue inside a body cavity of a patient without fully opening the patient, said method comprising the steps of:

inserting a cannula into the body cavity;

inserting, through the cannula, an instrument comprising a pair of relatively movable jaws hinged together at one end for pivotal movement about a first axis, each jaw having a row of spaced-apart, uniform-size teeth, each tooth having a base and a crest, the two rows being opposed and offset with respect to each other so that the rows of teeth mesh when the jaws are closed, the crest of each tooth having a channel therein running parallel to the direction of the row, all of the channels in each row being aligned so as to define at their bases a substantially straight needle passageway through all of the teeth in the rows, the pair of jaws being closed;

actuating an operating mechanism to first articulate the pair of jaws about a second pivot axis transverse to the first pivot axis and then actuate the first and second jaws to pivot about the first axis to an open position;

positioning the first and second jaws adjacent and transverse to the section of tubular tissue;

actuating the operating mechanism to pivot the first and second jaws to pivot about the first axis to clamp around the tissue and bend the clamped tissue into a wavelike configuration with a two-wall thickness of the tissue overlying the crest of each tooth, the tissue being forced deep enough into the spaces between the teeth that a first wall thickness of tissue, but not the second wall thickness thereof, protrudes into the needle passageway;

sliding a suturing cartridge having two needles attached to opposite ends of a length of bioabsorbable thread and loaded into a needle cartridge through a pathway in one of the jaws;

forcing the two needles completely through the needle passageways and the tissue, one needle for each passageway, thereby creating an encircling series of stitches in the wall of the tubular tissue; and detaching the needles from the thread and removing the needles from the body, thereby leaving a purse string suture in the tubular tissue, ready to be drawn snug and tied.

2. A method of placing a purse string suture according to claim 1, further comprising the step of providing a rotatable know bas the operating mechanism, and actuating the operating mechanism by rotating the know.

3. A surgical suturing instrument for placing a purse string suture in a tubular tissue, said instrument comprising:

a pair of relatively movable jaws for clamping the tubular tissue therebetween, a first jaw of said pair of jaws being pivotable with respect to a second jaw about a first pivot axis defined in said pair of jaws, each jaw having a row of spaced-part, uniform-size teeth;

actuating means, operably connected to said pair of jaws, for actuating said pair of jaws between an open position for receiving the tubular tissue and a clamping position where the row of teeth of said first jaw meshes with the row of teeth of said second jaw, wherein the clamping position is achieved by pivoting said pair of jaws about a second axis defined in one of said jaws and parallel to the first axis, wherein said actuating means includes a lost motion linkage having a lever pivotally connected to one of said jaws about the second pivot axis parallel to said first pivot axis, a link pivotally connected to said lever and a driving rod pivotally connected to said link, wherein said operating means slides said driving rod to actuate said pair of jaws about the first pivot axis and one of said jaws about the second pivot axis;

a camming rod slidably disposed between said pair of jaws and said actuating means to operate on at least one of said jaws and pivot said pair of laws about a third pivot axis transverse to the first pivot axis; and operating means, connected to said actuating means and said camming rod, for sliding said camming rod to articulate said pair of jaws about the third pivot axis and sliding said actuating means to actuate said pair of laws about the first pivot axis and one of said jaws about the second pivot axis.

4. A surgical suturing instrument according to claim 3, further comprising an elongated shaft for slidably housing said camming rod and said driving rod, said shaft being connected to said operating means at a first end and said pair of jaws at a second end.

5. A surgical suturing instrument according to claim 4, wherein said shaft includes stop means for limiting articulation of said pair of jaws.

6. A surgical suturing instrument according to claim 3, wherein each tooth includes a base and a crest, the two rows being opposed and offset with respect to each other in the clamping position so that the rows of teeth mesh when the jaws are closed, thereby bending the tubular tissue between the rows of teeth into a wavelike configuration with a two-wall thickness of the tissue overlying the crest of each tooth.

7. A surgical suturing instrument according to claim 6, wherein the crest of each tooth includes a channel therein running parallel to the direction of the row, all of the channels in each row being aligned so as to define at their bases a substantially straight passageway for the transit of a thread-pulling needle through all of the teeth in the row, the base of each channel being sufficiently close to the base of the tooth that a needle forced through the passageway when said jaws are clamped across the tissue can run through only the wall of the wave of tissue contacting and overlying the crest of each tooth without penetrating the next adjacent wall of the tissue.

8. A surgical suturing instrument according to claim 7, wherein the cross-section of the channel through each tooth is substantially keyhole-shaped, with a circular section at the base of the channel and a narrower-width slot section extending from the circular section of the crest of said tooth.

9. A surgical suturing instrument according to claim 6, wherein the width of each tooth, measured in the direction of the row of teeth, is greater at its base than at its crest.

10. A surgical suturing instrument according to claim 3, further comprising needle cartridge means for defining a needle guide, said cartridge means including an elongated body formed with two substantially parallel guideways for receiving first and second surgical needles for sliding movement therein, and an open channel joining said guideways throughout their length.

11. A surgical suturing instrument according to claim 10, wherein said needle cartridge is made of a flexible material and is insertable within a curved pathway in one of said jaws.

12. A surgical suturing instrument for placing a purse string suture in a tubular tissues, said instrument comprising:

a pair of relatively movable jaws for clamping the tubular tissue therebetween, a first jaw of said pair of jaws being pivotable with respect to a second jaw about a first pivot axis, each jaw having a row of spaced-apart, uniform-size teeth;

actuating means, operably connected to said pair of jaws, for actuating said pair of jaws between an open position for receiving the tubular tissue and a clamping position where the row of teeth of said first jaw meshes with the row of teeth of said second jaw;

a camming rod slidably diposed between said pair of jaws and said actuating means to operate on at least one of said jaws and pivot said pair of jaws about a second pivot axis transverse to the first pivot axis; and operating means, connected to said actuating means and said camming rod, for sliding said camming rod to articulate said pair of jaws about the second pivot axis and sliding said actuating means to actuate said pair of jaws about the first pivot axis; wherein said actuating means includes a lost motion linkage having a lever pivotally connected to one of said jaws about a third pivot axis parallel to said first pivot axis, a link pivotally connected to said lever and a driving rod pivotally connected to said link, and further comprising a first universal pin connecting said link with said lever and a second universal pin connecting said link with said driving rod, said first and second universal pins allowing said link to rotate about its longitudinal axis and relative to said lever and said driving rod.

13. A surgical suturing instrument for placing a purse string suture in a tubular tissue, said instrument comprising:

a pair of relatively movable jaws for clamping the tubular tissue therebetween, a first jaw of said pair of jaws being pivotable with respect to a second jaw about a first pivot axis, each jaw having a row of spaced-apart, uniform-size teeth;

actuating means, operably connected to said pair of jaws, for actuating said pair of jaws between an open position for receiving the tubular tissue and a clamping position where the row of teeth of said first jaw meshes with the row of teeth of said second jaw;

a camming rod slidably disposed between said pair of jaws and said actuating means to operate on at least one of said jaws and pivot said pair of jaws about a second pivot axis transverse to the first pivot axis;

operating means, connected to said actuating means and said camming rod, for sliding said camming rod to articulate said pair of jaws about the second pivot axis and sliding said actuating means to actuate said pair of jaws about the first pivot axis; and needle cartridge means for defining a needle guide, said cartridge means including an elongated body formed with two substantially parallel guideways for receiving first and second surgical needles for sliding movement therein, and an open channel joining said guideways throughout their length, wherein said needle cartridge is made of a flexible material and is insertable within a curved pathway in one of said jaws; and further comprising an elongated shaft having longitudinal notches for slidably housing said camming rod, said driving rod and said needle cartridge, said shaft being connected to said operating means at a first end and said pair of jaws at a second end, 14. A surgical suturing instrument for placing a purse string suture in a tubular tissue, said instrument comprising:
- a pair of relatively movable jaws for clamping the tubular tissue therebetween, a first jaw of said pair of jaws being pivotable with respect to a second jaw about a first pivot axis, each jaw having a row of spaced-apart, uniform-size teeth;
- actuating means, operably connected to said pair of jaws, for actuating said pair of jaws between an open position for receiving the tubular tissue and a clamping position where the row of teeth of said first jaw meshes with the row of teeth of said second jaw;
- a camming rod slidably disposed between said pair of jaws and said actuating means to operate on at least one of said jaws and pivot said pair of jaws about a second pivot axis transverse to the first pivot axis; and
- operating means, connected to said actuating means and said camming rod, for sliding said camming rod to articulate said pair of jaws about the second pivot axis and sliding said actuating means to actuate said pair of jaws about the first pivot axis, wherein
- said operating means includes a rotatable knob and motion imparting means for imparting rotational movement of said knob into linear movement of said camming rod and said driving rod.

15. A surgical suturing instrument according to claim 14, with said motion imparting means including an axially slidable actuating sleeve connected to said rotatable knob by mutually engagable threads.

16. A surgical suturing instrument according to claim 15, with said motion imparting means further including a first connecting rod operably connected to said driving rod and a second connecting rod operably connected to said camming rod, and first and second compression springs for biasing said first and second connecting rods in a rearward direction, with said actuating sleeve abutting and driving said first and second connecting rods in a forward direction when said rotatable knob is rotated in a first direction.

17. A surgical suturing instrument for placing purse string suture in a tubular tissue, said instrument comprising:
- a pair of relatively movable jaws for clamping the tubular tissue therebetween, a first jaw of said pair of jaws being pivotable with respect to a second jaw about a first pivot axis defined in said pair of jaws, each jaw having a row of spaced-apart. uniform-size teeth;
- actuating means, operably connected to said pair of jaws, for actuating said pair of jaws between an open position for receiving the tubular tissue and a clamping position where the row of teeth of said first jaw meshes with the row of teeth of said second jaw, wherein the clamping position is achieved by pivoting said pair of jaws about a second axis defined in one of said jaws and parallel to the first axis;
- a camming rod slidably disposed between said pair of jaws and said actuating means to operate on at least one of said jaws and pivot said pair of jaws about a third pivot axis transverse to the first pivot axis; and
- operating means, connected to said actuating means and said camming rod, for sliding said camming rod to articulate said pair of jaws about the third pivot axis and sliding said actuating means to actuate said pair of jaws about the first pivot axis and one of said jaws about the second pivot axis; and further comprising sealing means for providing an airtight seal within a cannula receiving the suturing instrument.

18. A surgical suturing instrument for placing a purse string suture in a tubular tissue, said instrument comprising:
- a pair of relatively movable jaws for clamping the tubular tissue therebetween, a first jaw of said pair of jaws being pivotable with respect to a second jaw about a first pivot axis defined in said pair of jaws, each jaw having a row of spaced-apart, uniform-size teeth;
- an actuating mechanism, operably connected to said pair of jaws, actuating said pair of jaws between an open position for receiving the tubular tissue and a clamping position where the row of teeth of said first jaw meshes with the row of teeth of said second jaw, said actuating mechanism including a lost motion linkage having a lever pivotally connected to one of said jaws about a second pivot axis defined in one of said jaws and parallel to said first pivot axis, a link pivotally connected to said lever and a driving rod pivotally connected to said link;
- a camming rod slidably disposed between said pair of jaws and said actuating mechanism to engage one of said jaws and pivot said pair of jaws about a third pivot axis transverse to the first pivot axis; and
- an operating mechanism operably connected to said actuating mechanism and said camming rod, said operating mechanism being actuated to slide said camming rod and articulate said pair of jaws about the third pivot axis transverse to the first pivot axis and to actuate said actuating mechanism to open and close said pair of jaws about the first pivot axis and to pivot one of said jaws about the second pivot axis to the clamping position.

19. A surgical suturing instrument according to claim 18, further comprising sealing means for providing an airtight seal within a cannula receiving the suturing instrument.

20. A surgical suturing instrument for placing a purse string suture in a tubular tissue, said instrument comprising:
- a pair of relatively movable jaws for clamping the tubular tissue therebetween, a first jaw of said pair of jaws being pivotable with respect to a second law about a first pivot axis defined in said pair of jaws, each jaw having a row of spaced-apart, uniform-size teeth;
- an actuating mechanism operably connected to said pair of jaws, actuating said pair of jaws between an open position for receiving the tubular tissue and a clamping position where the row of teeth of said first jaw meshes with the row of teeth of said second jaw, said actuating mechanism including a lost motion linkage having a lever pivotally connected to one of said jaws about a second pivot axis defined in one of said jaws and parallel to said first pivot axis, a link pivotally connected to said lever and a driving rod pivotally connected to said link;

a camming rod slidably disposed between said pair of jaws and said actuating mechanism to engage one of said jaws and pivot said pair of jaws about a third pivot axis transverse to the first pivot axis pin; and an operating mechanism operably connected to said actuating mechanism and said camming rod, said operating mechanism being actuated to slide said camming rod and articulate said pair of jaws about the third pivot axis transverse to the first pivot axis and to actuate said actuating mechanism to open and close said pair of jaws about the first pivot axis and to pivot one of said jaws about the second pivot axis to the clamping position, wherein said operating mechanism includes a rotatable knob and an axially slidable actuating sleeve connected to said rotatable knob by mutually engagable threads.

21. A surgical suturing instrument according to claim 20, wherein said operating mechanism further comprises a pivoting lever actuated by said sliding actuating sleeve.

22. A surgical suturing instrument according to claim 21, further comprising housing means for housing said rotatable knob, said actuating sleeve and said lever, said housing means including a stationary post for mounting said pivoting lever.

23. A surgical suturing instrument according to claim 22, wherein said operating means further comprises a first connecting rod operably connected to said driving rod and a second connecting rod operably connected to said camming rod, and first and second compression springs for biasing said first and second connecting rods in a rearward direction, with said actuating sleeve abutting and driving said first and second connecting rods in a forward direction when said rotatable knob is rotated in a first direction.

* * * * *